(12) United States Patent
Choi et al.

(10) Patent No.: US 7,612,887 B2
(45) Date of Patent: Nov. 3, 2009

(54) MICRO RESONATOR SENSOR

(75) Inventors: Young-Wan Choi, Seoul (KR); Doo-Gun Kim, Seoul (KR)

(73) Assignee: Chung-An University Industry-Academy Cooperation Foundation, Seoul (KR)

( * ) Notice: Subject to any disclaimer, the term of this patent is extended or adjusted under 35 U.S.C. 154(b) by 233 days.

(21) Appl. No.: 11/982,745

(22) Filed: Nov. 5, 2007

(65) Prior Publication Data

US 2008/0266573 A1 Oct. 30, 2008

(30) Foreign Application Priority Data

Nov. 3, 2006 (KR) .................. 10-2006-0108579

(51) Int. Cl.
*G01C 3/14* (2006.01)
*G01B 9/02* (2006.01)
(52) U.S. Cl. ......................... 356/481; 385/12
(58) Field of Classification Search ................ 356/481, 356/517; 385/12
See application file for complete search history.

(56) References Cited

U.S. PATENT DOCUMENTS

2005/0035278 A1 2/2005 Margalit et al.
2009/0028492 A1* 1/2009 Wu et al. ...................... 385/14

FOREIGN PATENT DOCUMENTS

| EP | 1528389 | 5/2005 |
| KR | 1020050102391 | 10/2005 |
| KR | 1020060089103 | 8/2006 |
| KR | 1020060092348 | 8/2006 |
| WO | WO2005/119217 | 12/2005 |

* cited by examiner

*Primary Examiner*—Patrick J Connolly
(74) *Attorney, Agent, or Firm*—Occhiuti Rohlicek & Tsao LLP

(57) ABSTRACT

A micro resonator sensor includes a main waveguide, a resonance waveguide and optical path changing means. Optical path changing means are installed at apex regions contacting with adjacent optical waveguides forming the resonance waveguide and reflect at least a part of the split optical signal inputted into the resonance waveguide to circulate the split optical signal inside the resonance waveguide. The micro resonator sensor can be manufactured without an excessive radiation loss and can be manufactured as an on-chip.

20 Claims, 13 Drawing Sheets

MICRO RESONATOR SENSOR

CROSS-REFERENCE TO RELATED APPLICATIONS

This application claims the benefit of priority of Korean Patent Application No. 10-2006-0108579 filed on Nov. 3, 2006, which are incorporated by reference in their entirety herein.

BACKGROUND

1. Technical Field

The present invention relates to a micro resonator sensor, and more specifically, to a sensor for detecting a characteristic of a material to be measured (also called "to-be-measured material") using changes in a refractive index of a resonator.

2. Related Art

Generally, a resonator sensor serves to detect a characteristic of a measured-material by detecting intensity of light at the output terminal of a waveguide that is formed with an input terminal and an output terminal. In this case, the intensity of light corresponds to a change of an effective refractive index of a ring resonator that occurs when light traveling through the waveguide is coupled to the ring resonator installed to be spaced apart from the waveguide.

FIG. 1 is a view showing a conventional micro ring resonator sensor.

Referring to FIG. 1, a conventional micro ring resonator comprises a main waveguide 110 and a ring resonator 120. The main waveguide 110 is constructed with an optical fiber or an optical waveguide, and both ends of the main waveguide 110 respectively function as an input terminal for receiving optical signals and an output terminal for outputting optical signals. The ring resonator 120 is an optical fiber or an optical waveguide of a ring shape having a predetermined radius R, and the ring resonator 120 has an opening 122 whose surface is interface-processed so that light passing through the optical fiber or the optical waveguide forming the ring resonator 120 may effectively react with liquid or gas, which is a measured-material. The opening 122 is formed on the top or a side surface of the optical fiber or the optical waveguide configuring the ring resonator 120. An optical transfer mode that can be accepted by the micro ring resonator sensor is determined depending on the position of the opening 122. Accordingly, if the opening 122 is formed on both of the top and side surfaces of the ring resonator 120, optical signals of both TM and TE modes can be received. The main waveguide 110 and the ring resonator 120 are arranged on one dielectric substrate to be spaced apart from each other to configure a ring resonator sensor.

As shown in FIG. 1, in the conventional micro ring resonator sensor, an optical signal inputted through the input terminal of the main waveguide 110 advances along the main waveguide 110 and is coupled to the ring resonator 120 depending on a resonance condition of the ring resonator 120 that is arranged to be spaced apart from the main waveguide 110. At this point, the light inputted into the ring resonator 120 reacts with a bio-material in a liquid or gaseous state, which is a measured-material, on the interface-processed surface of the opening 122 formed at the ring resonator 120, and thus the effective refractive index of the ring resonator 120 is changed. Then, as the effective refractive index of the ring resonator 120 is changed, a condition for optical coupling from the main waveguide 110 to the ring resonator 120 is changed. At this point, the effective refractive index of the ring resonator 120 is changed in correspondence with concentration of the material reacting on the top and side surfaces of the ring resonator 120. Accordingly, the amount of light outputted through the output terminal of the main waveguide 110 is changed, and thus the characteristic of the material can be detected. In this manner, if a bio-transducer is configured by employing a biological element at the opening 122 of the ring resonator 120, a bio-sensor using a ring resonator can be manufactured.

Since any reflection does not occur inside of the ring resonator 120 of the convention micro ring resonator sensor having four ports a1, a2, a3, and a4 shown in FIG. 1, the initial condition is b1=b3=a2=a4=zero. Accordingly, the characteristic function of the micro ring resonator sensor shown in FIG. 1 is expressed as shown in the following Equation.

$$\begin{vmatrix} b_1 \\ b_2 \\ b_3 \\ b_4 \end{vmatrix}_K = \begin{vmatrix} 0 & \sqrt{1-k^2} & 0 & jk \\ \sqrt{1-k^2} & 0 & jk & 0 \\ 0 & jk & 0 & \sqrt{1-k^2} \\ jk & 0 & \sqrt{1-k^2} & 0 \end{vmatrix}_K \begin{vmatrix} a_1 \\ a_2 \\ a_3 \\ a_4 \end{vmatrix}_K \quad \text{[Equation 1]}$$

In Equation 1, $|k^2|$ is intensity of an optical signal coupled from port 1 a1 to port 4 b4 when the light signal passes through the optical waveguide once, and $|1-k^2|$ is intensity of an optical signal passing through without being coupled when the light signal passes through the optical waveguide once.

In addition, the optical signal inside of the ring resonator can be expressed in the following Equation.

$$a_3 = b_4 e^{-(\alpha_R + j\phi_R)} \quad \text{[Equation 2]}$$

In Equation 2, $\alpha_R$ is a loss occurred when the optical signal passes through inside of the ring resonator once, and $\phi_R$ is a phase difference occurred when the optical signal passes through inside of the ring resonator once.

On the other hand, the following expression can be obtained from Equation 1.

$$b_1 = \sqrt{1-k^2}\, a_2 + jka_4$$

$$b_2 = \sqrt{1-k^2}\, a_1 + jka_3$$

$$b_3 = jka_2 + \sqrt{1-k^2}\, a_4$$

$$b_4 = jka_1 + \sqrt{1-k^2}\, a_3 \quad \text{[Equation 3]}$$

In addition, the following expression is derived from Equations 2 and 3.

$$b_2 = \left[ \frac{\sqrt{1-k^2} - e^{-(\alpha_R + j\phi_R)}}{1 - \sqrt{1-k^2}\, e^{-(\alpha_R + j\phi_R)}} \right] a_1 \quad \text{[Equation 4]}$$

Then, resonance of the ring occurs when $\phi = 2m\pi$ in Equation 4, and at this point, Equation 4 is rearranged as shown below.

$$\frac{b_2}{a_1} = \left[ \frac{\sqrt{1-k^2} - e^{-\alpha_R}}{1 - \sqrt{1-k^2}\, e^{-\alpha_R}} \right] a_1 \quad \text{[Equation 5]}$$

If a resonance condition defined as shown in Equation 5 occurs, a coupling occurs from the main waveguide 110 to the ring resonator 120, and since a critical coupling condition is satisfied when a condition such as the Equation shown below is satisfied, an optical signal is not outputted to the output terminal of the main waveguide 110. At the time point when the critical coupling condition is satisfied, intensity of the optical signal coupled from the main waveguide 110 to the ring resonator 120 becomes the maximum.

$$\sqrt{1-k^2}=e^{-\alpha R}$$ [Equation 6]

In a resonance state, the critical coupling condition is determined by adjusting the coupling coefficient k and the loss coefficient $\alpha_R$. At this point, the coupling coefficient k is determined by a distance spaced between the main waveguide 110 and the ring resonator 120, and the loss coefficient $\alpha_R$ is determined by a reaction of the optical signal and the bio-material at the opening 122 formed at the ring resonator 120.

FIG. 2 is a view showing an example of a characteristic curve of an output light corresponding to the wavelength of an incident light in accordance with a resonance condition of the ring resonator 20 when an optical signal is inputted into the main waveguide 110.

Referring to FIG. 2, if a critical coupling occurs under the resonance condition of the ring resonator 120, an output is not occurred at the output terminal of the main waveguide 110 at the minimum wavelength, and here, the minimum wavelength is moved by interactions among bio-molecules. That is, the wavelength of an optical signal at which an output is not occurred at the output terminal of the main waveguide 110 is changed in accordance with the variation of the effective refractive index of the ring resonator 120 invited by a measured-material contacting with the opening 122 of the ring resonator 120.

Referring to FIG. 2, it is understood that whenever the effective refractive index of the ring resonator 120 is increased by $1 \times 10^{-4}$, the minimum wavelength at which an output is not occurred at the output terminal of the main waveguide 110 is constantly increased. Accordingly, the ring resonator sensor can detect a characteristic of a measured-material by detecting a response signal for the intensity and wavelength of an optical signal outputted through the output terminal of the main waveguide 110.

On the other hand, the output of the ring resonator sensor is very sensitive to the change of the dielectric constant of a medium that occurs when the medium is in contact with the opening 122 formed at the ring resonator 120. That is, the dielectric constant of the medium changes as the medium flows through the opening 122 of the ring resonator sensor, and accordingly, the effective refractive index of the ring resonator 120 is changed. Such a change of the effective refractive index of the ring resonator 120 invites a change in a resonance condition, and thus the wavelength of the output signal is moved. Accordingly, the ring resonator sensor detects a characteristic of a measured-material by grasping concentration of the measured-material through the effective refractive index of the ring resonator 120 calculated based on the intensity and phase of the optical signal measured at the output terminal of the main waveguide 110.

The ring resonator sensor described above can be implemented in the form of a bio-sensor, in which while a bio-molecule among bio-molecules combined to each other is fixed on the surface of the opening 122 formed at the ring resonator sensor, a bio-molecule corresponding to the fixed bio-molecule as a measured-material is in contact with the surface of the opening 122, and then a bonding activity between them is detected. Examples of the bio-molecules bonding to each other include antibody-antigen, hormone-receptor, protein-protein, DNA-DNA, DNA-protein, and the like. The bio-sensor that uses a ring resonator like this is a sensor where a ligand is fixated on the surface of the opening 122 of the ring resonator sensor. A method of chemically adsorbing a thiolized ligand on a metal surface can be an example of a method of fixating the ligand, in which the ligand is thiolized by bonding a thiol group to the ligand through a covalent bond. In addition, there also is a method of fixating the ligand on the surface of the opening 122 of the ring resonator sensor using a hydrogel matrix configured in a carboxyl-methylated dextran chain. Such a ring resonator sensor is most advantageous in that a molecule can be directly measured without using an indicator material, such as a radio-active material or a fluorescent material. Furthermore, if a ring resonator bio-sensor is used, a process of bonding bio-molecules can be monitored in real-time.

However, although the ring resonator sensor is advantageous in that a characteristic of a measured-material can be measured with a simple configuration, there is a certain limit in the aspect of miniaturizing the sensor. That is, in the case of a conventional ring resonator sensor provided with a resonator where a waveguide is formed in a loop shape of a circular form, it needs to deeply etch a neighborhood of an optical waveguide configuring the ring resonator in order to reduce the radius of the ring resonator without an excessive radiation loss. If the neighborhood of the optical waveguide configuring the ring resonator is deeply etched, although the effect of optical confinement on the side surface of the optical waveguide can be enhanced, there is a problem in that the optical propagation loss is increased due to sidewall roughness. In addition, if the optical waveguide forming the ring resonator is made of an intrinsic material, etching through the intrinsic material brings about a problem appeared due to excessive surface recombination. Furthermore, such a ring resonator invites increase of radiation loss and acts as an obstacle to miniaturization of the ring resonator sensor as a result.

SUMMARY

It is an object of the invention to provide a high-sensitive super-micro resonator sensor, which is integrated as an on-chip to be used whenever and wherever, while minimizing radiation loss incurred by miniaturization of the sensor.

According to one aspect of the invention, there is provided a micro resonator sensor comprising a main waveguide provided with an incident hole for receiving an optical signal and an exit hole for outputting an optical signal, the main waveguide having an optical coupling region where a part of the optical signal inputted through the incident hole is split; a resonance waveguide having an optical coupling region optically connected to the optical coupling region of the main waveguide to receive the split optical signal split from the main waveguide, the resonance waveguide being configured of a plurality of optical waveguides arranged in a polygonal shape and optical path changing means installed at apex regions contacting with adjacent optical waveguides forming the resonance waveguide, for reflecting at least a part of the split optical signal inputted into the resonance waveguide to circulate the split optical signal inside the resonance waveguide, wherein openings are formed at one or more optical waveguides among optical waveguides configuring the resonance waveguide.

According to another aspect of the invention, there is provided a micro resonator sensor comprising a first main waveguide provided with an incident hole for receiving an optical signal and an exit hole for outputting an optical signal, having an optical coupling region where a part of the optical signal inputted through the incident hole is split, a first resonance waveguide having an optical coupling region optically connected to the optical coupling region of the first main waveguide to receive the split optical signal split from the first main waveguide, the first resonance waveguide being configured of a plurality of optical waveguides arranged in a polygonal shape, a second main waveguide provided with an incident hole for receiving an optical signal and an exit hole for outputting an optical signal, the second main waveguide having an optical coupling region where a part of the optical signal inputted through the incident hole is split, a second resonance waveguide having an optical coupling region optically connected to the optical coupling region of the second main waveguide for receiving the split optical signal split from the second main waveguide, the second resonance waveguide being configured of a plurality of optical waveguides arranged in a polygonal shape and optical path changing means installed at apex regions contacting with adjacent optical waveguides forming the first and second resonance waveguides, for reflecting at least a part of the split optical signal inputted into the first or second resonance waveguide to circulate the split optical signal inside the first and second resonance waveguides, wherein the first and second resonance waveguides form a single resonance path by sharing one apex, and openings are formed at one or more optical waveguides among optical waveguides configuring the first and second resonance waveguides.

BRIEF DESCRIPTION OF THE DRAWINGS

Further objects and advantages of the invention can be more fully understood from the following detailed description taken in conjunction with the accompanying drawings in which.

DESCRIPTION OF EXEMPLARY EMBODIMENTS

Hereinafter, preferred embodiments of a micro resonator sensor according to the present invention will be described in detail with reference to the accompanying drawings.

Figure 1:
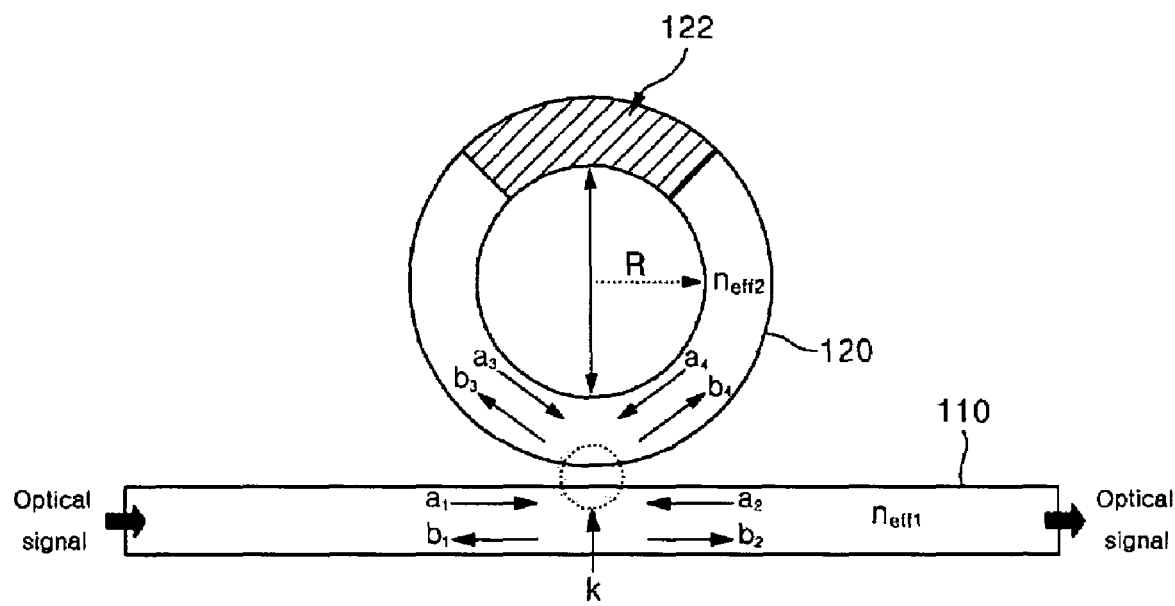
FIG. 1 is a view showing a conventional micro ring resonator sensor.
Figure 2:
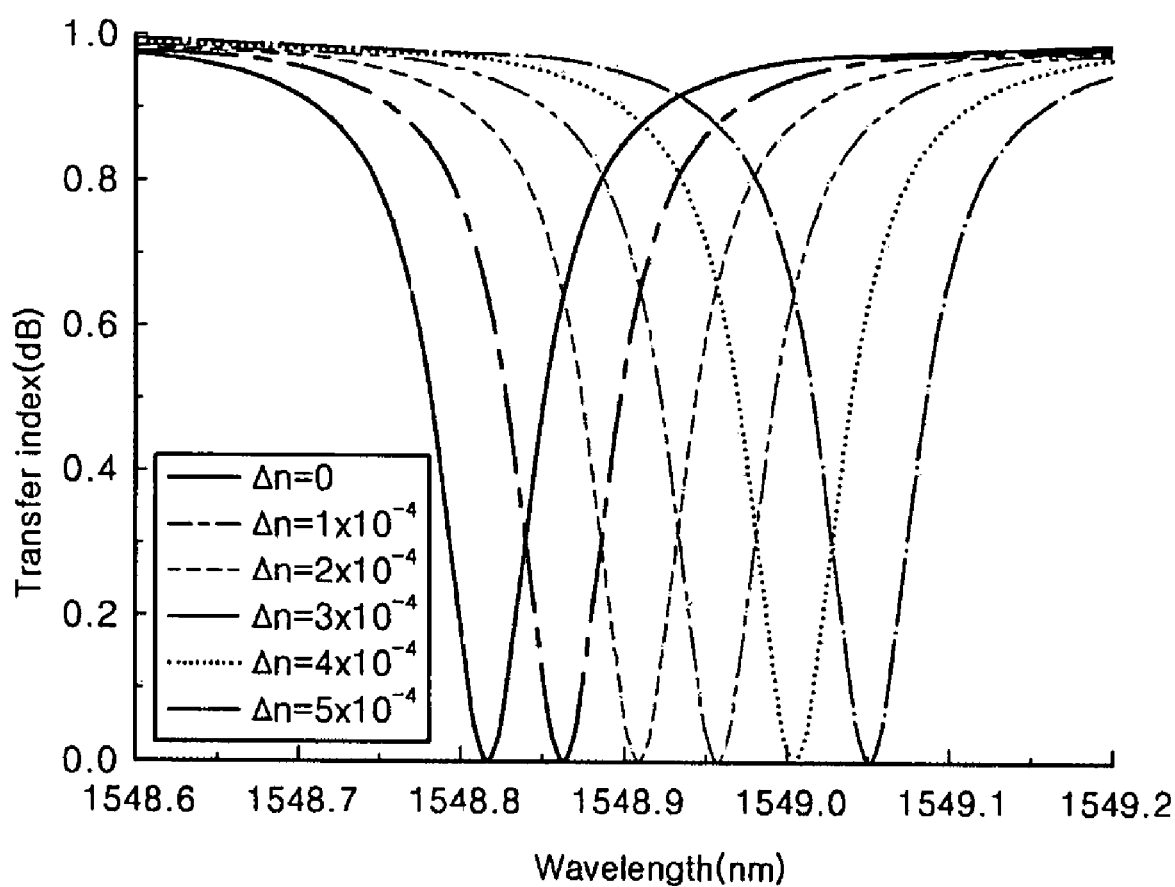
FIG. 2 is a view showing an example of a characteristic curve of an output light in accordance with a resonance condition of a ring resonator in the conventional micro ring resonator sensor.
Figure 3:
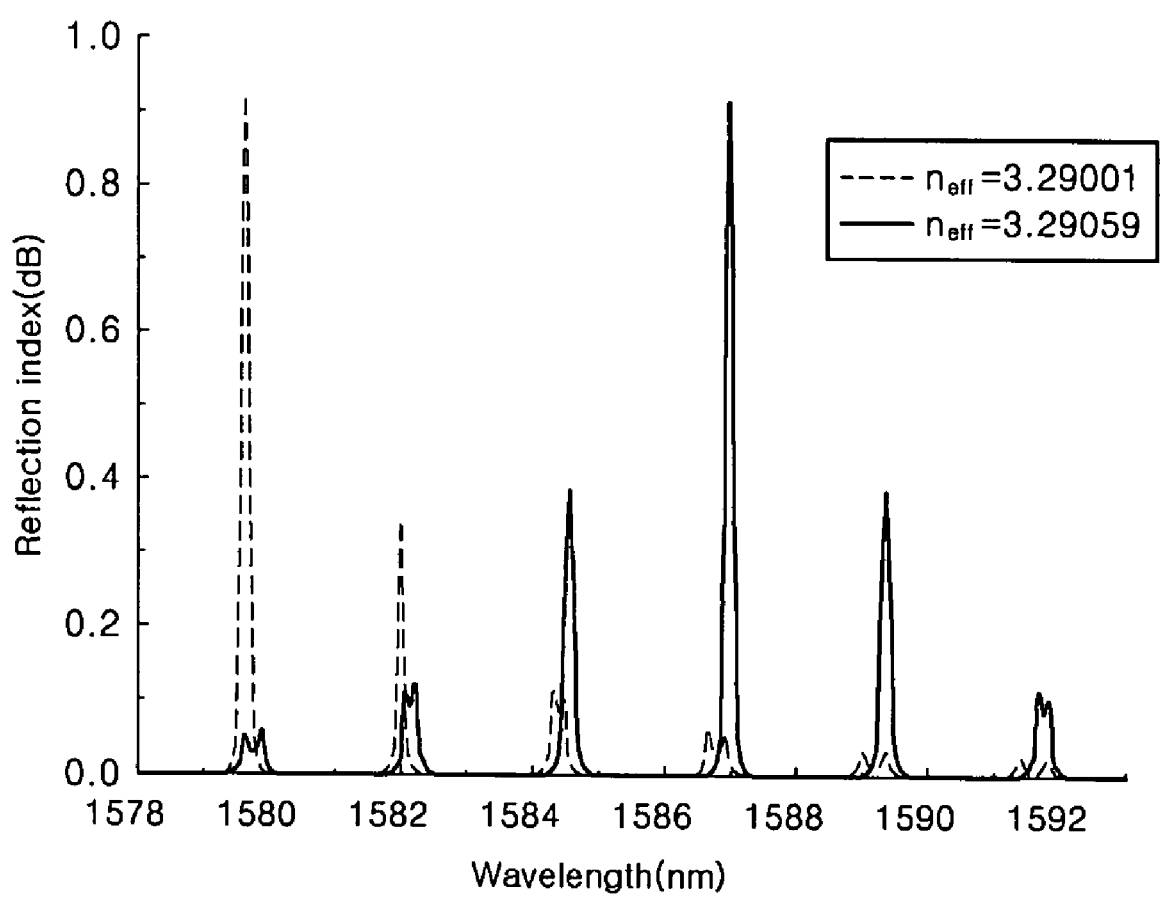
FIG. 3 is a view showing a reflection spectrum measured when the refraction index of a resonance ring at one side is set to 3.29001 and 3.29059 while a resonance ring at the other side is fixed in the conventional micro ring resonator sensor.
Figure 4:
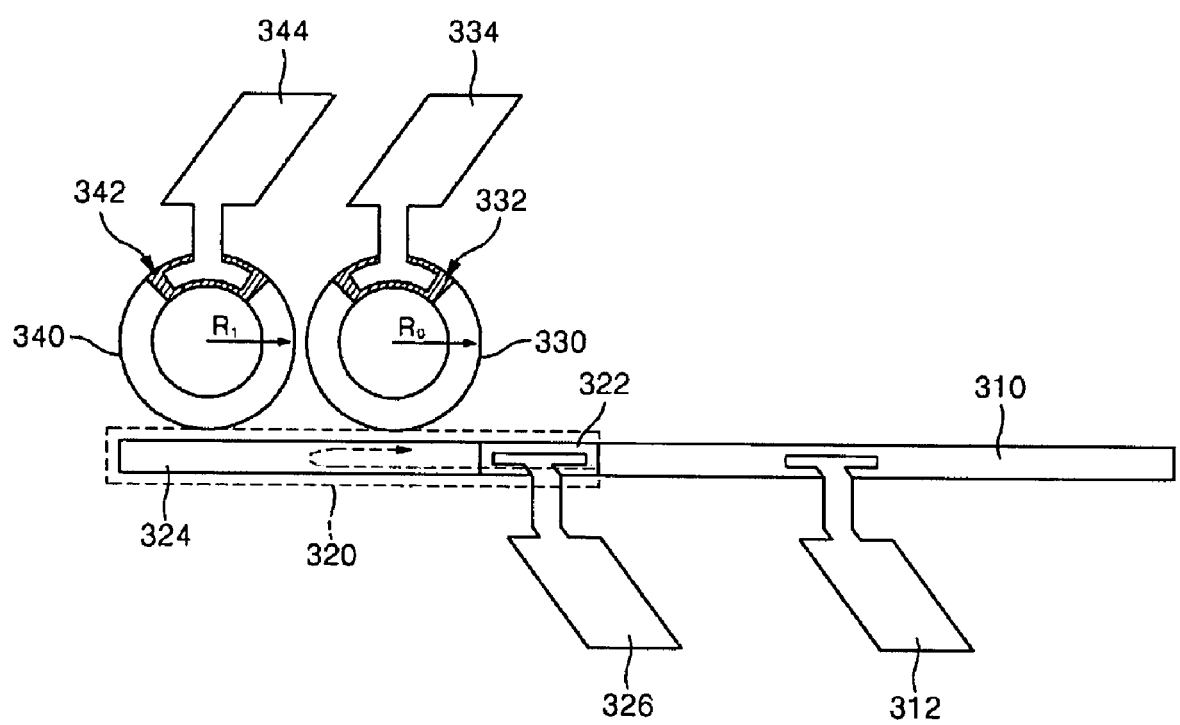
FIG. 4 is a view showing an example of a variable wavelength optical source employed in a micro resonator sensor according to the present invention.

FIG. 4 is a view showing an example of a variable wavelength optical source employed in a micro resonator sensor according to the present invention.

Referring to FIG. 4, the variable wavelength optical source varies the wavelength of an optical signal radiated from an optical source, such as a laser diode, into a signal of a desired wavelength and provides the signal to the main waveguide of the micro resonator sensor. The variable wavelength optical source comprises a light generation unit 410, an optical waveguide 420, a first resonance ring 430, and a second resonance ring 440.

The light generation unit 410 is a laser diode for generating optical signals of a predetermined wavelength by current or voltage inputted from outside through an electrode 412. The optical waveguide 420 is arranged to be spaced apart from the first resonance ring 430 and the second resonance ring 440 by a certain distance. Coupling coefficients between the optical waveguide and each of the resonance rings 430 and 440 are changed depending on the spaced distances between the optical waveguide and each of the resonance rings 430 and 440, and thus the amount of optical signals coupling with each other is changed. Such an optical waveguide 420 comprises a phase control region 422 and a reflection region 424, and an electrode 426 is connected in the phase control region 422 to control the phase of an optical signal by changing the refractive index based on the current and voltage inputted into the phase control region 422. The optical signal radiated from the light generation unit 410 and inputted into the optical waveguide 420 is coupled to the first resonance ring 430 and forms a first optical wave flowing clockwise within the first resonance ring 430. In addition, the first optical wave is coupled to the second resonance ring 440 and forms a second optical wave flowing counterclockwise within the second resonance ring 440. Such a first optical wave and a second optical wave are coupled to the optical waveguide 420 in the reflection region 424 of the optical waveguide 420 and advance to the light generation unit 410. Then, the optical waves are added to an optical signal generated by the light generation unit 410, and the wavelength of the finally radiated optical signal is changed.

The first resonance ring 430 and the second resonance ring 440 are manufactured by configuring an optical fiber or an optical waveguide in a circular shape, in which phase control regions 432 and 442 where the refractive index is changed depending on the amount of drive current supplied from outside are formed. The first resonance ring 430 and the second resonance ring 440 are optically connected to exchange optical signals with each other. In addition, radiuses $R_0$ and $R_1$ of the first resonance ring 430 and the second resonance ring 440 are set to be different from each other. Therefore, since the circulation distance of an optical signal within each of the resonance rings 430 and 440 becomes different from those of others, the resonance wavelength of each of the resonance rings 430 and 440 becomes different from other resonance wavelengths. If the amount of current inputted into one of the resonance rings (e.g., the resonance ring of reference number 430) is changed in this state, and thus changes the refractive index of the corresponding resonance ring 430, the two rings are simultaneously resonated at a specific wavelength by a Vernier effect, and an intense reflection is induced. That is, if the refractive index of one resonance ring 430 is fixed, and the refractive index of the other resonance ring 440 is gradually increased or decreased, peaks of the reflective index appear one by one at wavelengths increased or decreased by integer times of a free spectral range (FSR).

If the variable wavelength optical source described above referring to FIG. 4 is applied to a micro resonator sensor according to the present invention, all constitutional elements of the sensor can be integrated on a single wafer, and thus the micro resonator sensor can be manufactured in the form of a photonic integrated circuit. Therefore, the micro resonator sensor can be further simply manufactured at a low price. In addition, other than the variable wavelength optical source described referring to FIG. 4, a well-known light emitting element such as a laser diode can be applied as an optical source of the micro resonator sensor according to the present invention.

Figure 5:
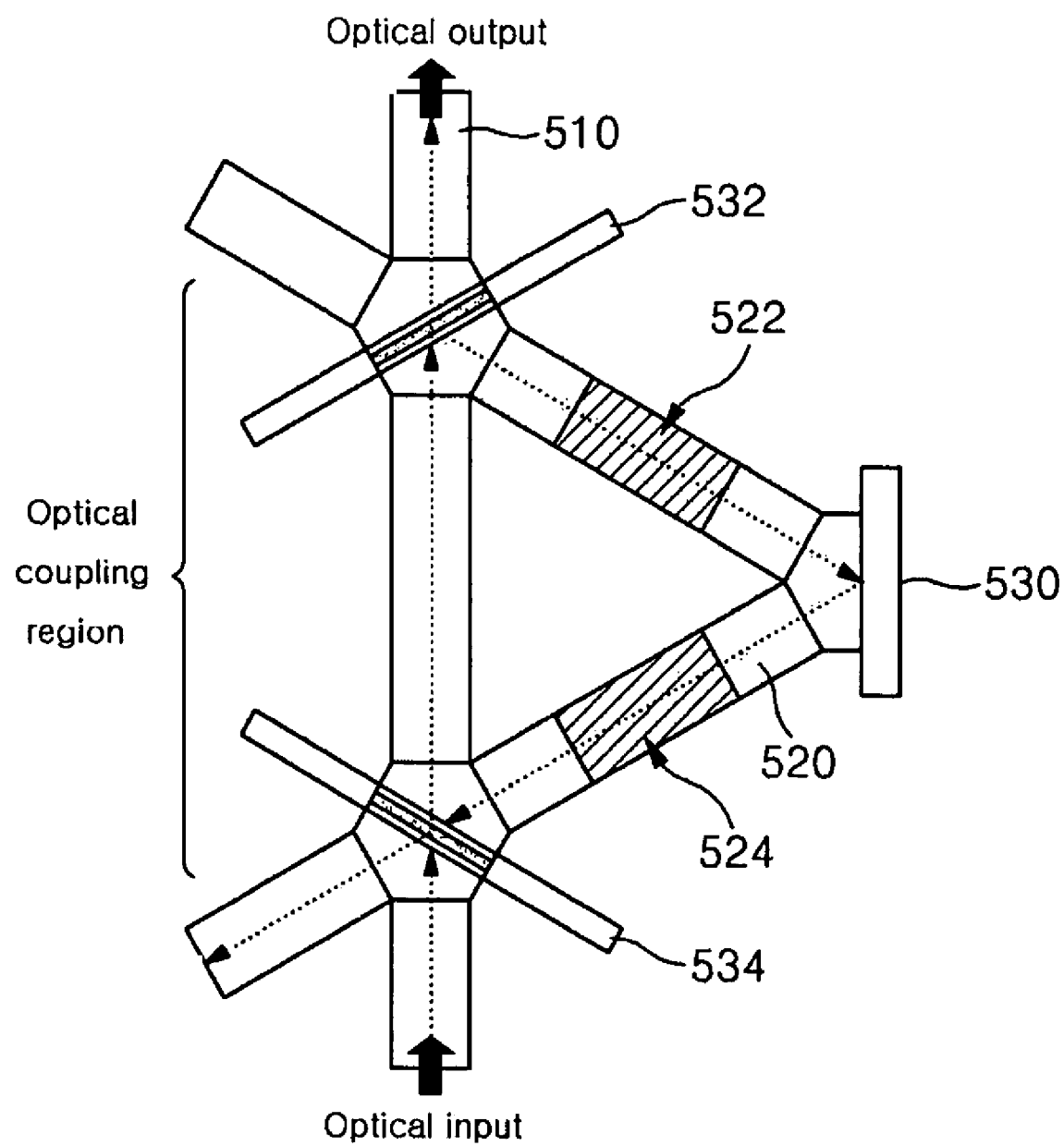
FIG. 5 is a view showing the configuration of a micro resonator sensor according to a first embodiment of the invention.

FIG. 5 is a view showing the configuration of a micro resonator sensor according to a first embodiment of the invention.

Referring to FIG. 5, the micro resonator sensor according to a first embodiment of the invention comprises a main waveguide 510, a resonance waveguide 520, a total reflection mirror 530, and beam splitters 532 and 534. The main waveguide 510 has an incident hole for receiving an optical signal and an exit hole for outputting an optical signal, and an optical coupling region where an optical signal inputted through the incident hole is coupled to the resonance waveguide 520 is formed at the main waveguide 510. The resonance waveguide 520 has an optical coupling region optically connected to the optical coupling region of the main waveguide 510, for receiving an optical signal coupled to the resonance waveguide 520 (hereinafter, referred to as a split optical signal) among the optical signal inputted through the incident hole of the main waveguide 510 in which a plurality of optical waveguides is arranged in a triangular shape. At this point, one of optical waveguides configuring three sides of the resonance waveguide 520 of a triangular shape is formed as a single body together with an optical waveguide configuring the main waveguide 510. The beam splitters 532 and 534 are arranged at the positions where two optical waveguides among the optical waveguides configuring the three sides of the resonance waveguide 520 of a triangular shape, other than the one optical waveguide formed as a single body together with the optical waveguide configuring the main waveguide 510, are connected to the main waveguide 510. In addition, the total reflection mirror 530 is arranged at the position where the two optical waveguides, other than the one optical waveguide formed as a single body together with the optical waveguide configuring the main waveguide 510, are connected to each other.

After passing through a second beam splitter 534, the optical signal inputted through the incident hole of the main waveguide 510 is split by a first beam splitter, outputted through the exit hole of the main waveguide 510, and simultaneously, inputted into the resonance waveguide 520. The split optical signal inputted into the resonance waveguide 520 is reflected by the total reflection mirror 530 and subsequently split by the second beam splitter 534, and a part of the optical signal advances toward a monitoring unit (not shown), and a part of the optical signal advances toward the exit hole of the main waveguide 510. In this manner, the split optical signal inputted into the resonance waveguide 520 circulates inside the resonance waveguide 520.

On the other hand, openings 522 and 524 are formed on at least one of the top surface and the side surfaces of at least one of two optical waveguides among the optical waveguides configuring the resonance waveguide 520, other than the optical waveguide formed as a single body together with the optical waveguide configuring the main waveguide 510. The optical signal inputted through the incident hole of the main waveguide 510 is coupled to the resonance waveguide 520 by the first beam splitter 532, and the coupled split optical signal reacts with a measured-material of a liquid or gaseous state at the openings 522 and 524 formed at the resonance waveguide 520. The effective refractive index of the resonance waveguide 520 is changed by the reaction of the split optical signal and the measured-material, and accordingly, the phase of the optical signal is changed, and thus a coupling resonance condition is changed. The resonance condition of the resonance waveguide 520 and the critical coupling condition in a resonance state are as shown in Equations 5 and 6. As described above, since the resonance condition of the resonance waveguide 520 is changed in correspondence with concentration of the measured-material reacting at the interface of the openings 522 and 524 of the resonance waveguide 520, if intensity of the optical signal outputted through the exit hole of the main waveguide 510 is measured, a characteristic of the measured-material can be detected.

Figure 6:
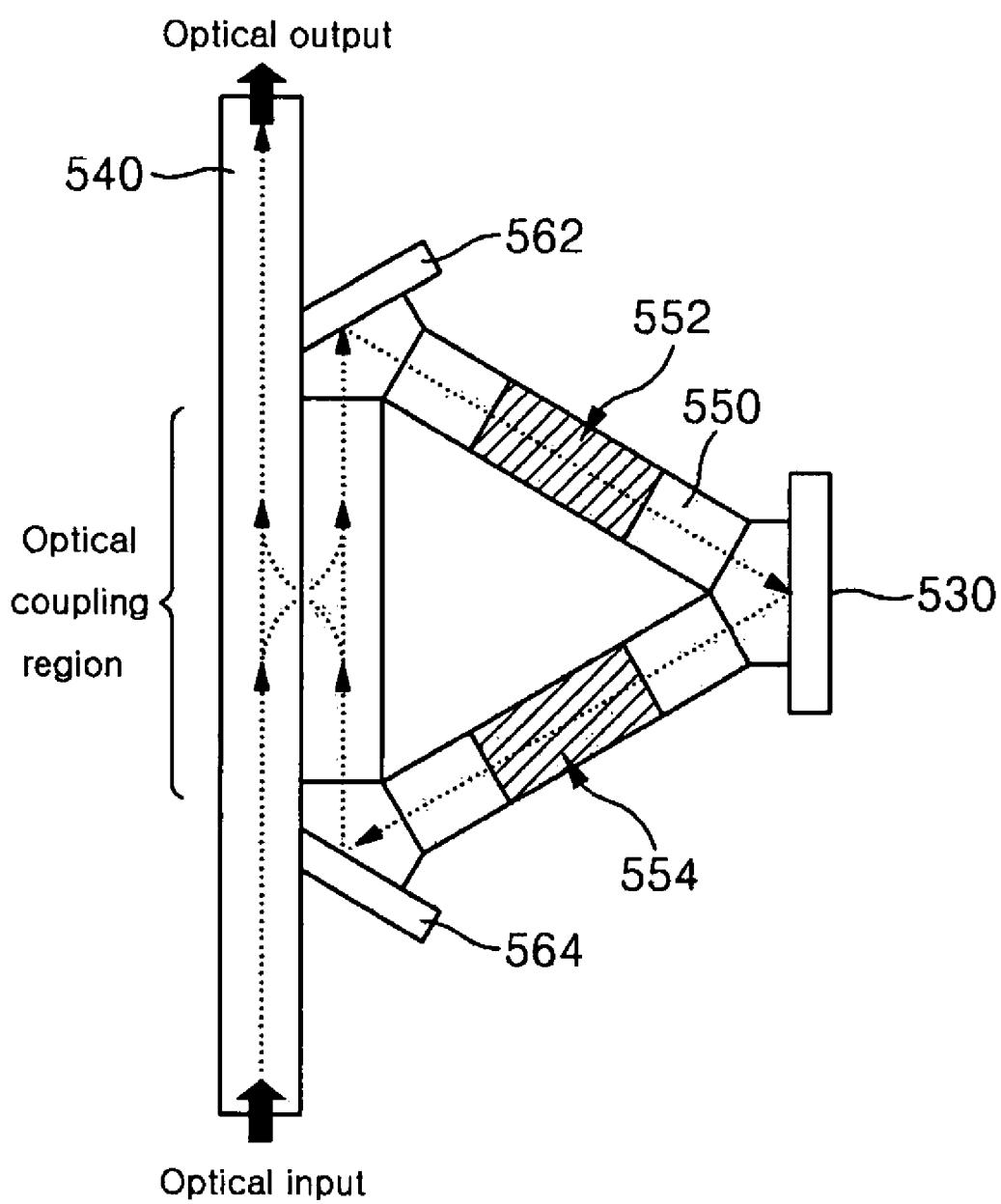
FIG. 6 is a view showing the configuration of a micro resonator sensor according to a second embodiment of the invention.

FIG. 6 is a view showing the configuration of a micro resonator sensor according to a second embodiment of the invention.

Referring to FIG. 6, the micro resonator sensor according to a second embodiment of the invention comprises a main waveguide 540, a resonance waveguide 550, and total reflection mirrors 560, 562, and 564. The main waveguide 540 has an incident hole for receiving an optical signal and an exit hole for outputting an optical signal, and an optical coupling region where the optical signal inputted through the incident hole is coupled to the resonance waveguide 550 is formed at the main waveguide 540. The resonance waveguide 550 has an optical coupling region optically connected to the optical coupling region of the main waveguide 540, for receiving an optical signal coupled to the resonance waveguide 550 among the optical signal inputted through the incident hole of the main waveguide 540, and a plurality of optical waveguides is arranged in a triangular shape. At this point, one of optical waveguides configuring three sides of the resonance waveguide 550 of a triangular shape is arranged in parallel with the main waveguide 540. The total reflection mirrors 560, 562, and 564 are arranged at apex regions where the optical waveguides configuring three sides of the resonance waveguide 550 are connected to each other.

On the other hand, openings 552 and 554 are formed on at least one of the top surface and the side surfaces of at least one of two optical waveguides among the optical waveguides configuring the resonance waveguide 550, other than the optical waveguide arranged in parallel with the optical waveguide configuring the main waveguide 540. The optical signal inputted through the incident hole of the main waveguide 540 is coupled to the resonance waveguide 550 in the optical coupling region. The optical signal inputted into the resonance waveguide 550 is reflected by the total reflection mirrors 560, 562, and 564 installed at the respective apexes of the resonance waveguide 550 and travels clockwise inside the resonance waveguide 550. At this time, the optical signal traveling inside the resonance waveguide 550 reacts with a measured-material of a liquid or gaseous state at the openings 552 and 554 formed at the resonance waveguide 550. Accordingly, the effective refractive index of the resonance waveguide 550 is changed by the reaction of the split optical signal and the measured-material, and accordingly, the phase of the optical signal is changed, and thus a coupling resonance condition is changed. Subsequently, the optical signal traveling inside the resonance waveguide 550 is coupled to the main waveguide 540 in the optical coupling region of the resonance waveguide 550 and outputted through the exit hole of the main waveguide 540. As described above, since the resonance condition of the resonance waveguide 550 is changed in correspondence with concentration of the measured-material reacting at the interface of the openings 552 or 554 of the resonance waveguide 550, if intensity of the optical signal outputted through the exit hole of the main waveguide 540 is measured, a characteristic of the measured-material can be detected.

Figure 7:
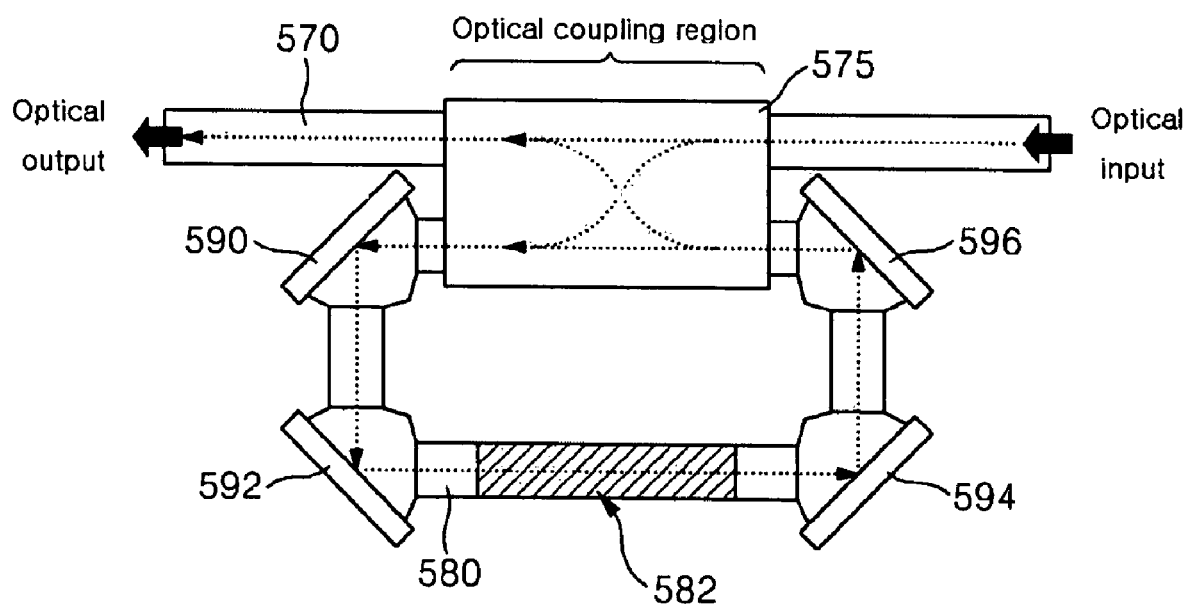
FIG. 7 is a view showing the configuration of a micro resonator sensor according to a third embodiment of the invention.

FIG. 7 is a view showing the configuration of a micro resonator sensor according to a third embodiment of the invention.

Referring to FIG. 7, the micro resonator sensor according to a third embodiment of the invention comprises a main waveguide 570, an optical coupler 575, a resonance waveguide 580, and total reflection mirrors 590, 592, 594, and 596. The main waveguide 570 has an incident hole for receiving an optical signal and an exit hole for outputting an optical signal, and an optical coupling region where the optical signal inputted through the incident hole is coupled to the optical coupler 575 is formed at the main waveguide 570. The optical coupler 575 splits the optical signal inputted through the incident hole of the main waveguide 570 to the exit hole of the main waveguide 570 and the resonance waveguide 580. In addition, the optical coupler 575 splits the optical signal that has circulated inside the resonance waveguide 580 to the exit hole of the main waveguide 570 and to the resonance waveguide 580. If a multi-mode interference coupler (MMIC) using a self imaging phenomenon is applied as the optical coupler 575, it is advantageous in that the overall size of the micro resonator sensor can be reduced, and the optical coupler 575 and the other elements can be easily implemented on a single wafer.

The resonance waveguide 580 has an optical coupling region optically connected to the optical coupler 575, for receiving an optical signal coupled to the resonance waveguide 580 among the optical signal inputted through the incident hole of the main waveguide 570, and a plurality of optical waveguides is arranged in a rectangular shape. At this point, one of optical waveguides configuring four sides of the resonance waveguide 580 of a rectangular shape is connected to the optical coupler 575. The total reflection mirrors 590, 592, 594, and 596 are arranged at apex regions where the optical waveguides configuring four sides of the resonance waveguide 580 are connected to each other.

On the other hand, an opening 582 is formed on at least one of the top surface and the side surfaces of at least one of three optical waveguides among the optical waveguides configuring the resonance waveguide 580, other than the optical waveguide connected to the optical coupler 575. The optical signal inputted through the incident hole of the main waveguide 570 is coupled to the resonance waveguide 580 through the optical coupler 575. The optical signal inputted into the resonance waveguide 580 is reflected by the total reflection mirrors 590, 592, 594, and 596 installed at the respective apexes of the resonance waveguide 580 and travels counterclockwise inside the resonance waveguide 580. At this time, the optical signal traveling inside the resonance waveguide 580 reacts with a measured-material of a liquid or gaseous state at the opening 582 formed at the resonance waveguide 580. Accordingly, the effective refractive index of the resonance waveguide 580 is changed by the reaction of the split optical signal and the measured-material, and accordingly, the phase of the optical signal is changed, and thus a coupling resonance condition is changed. Subsequently, the optical signal traveling inside the resonance waveguide 580 is coupled to the main waveguide 570 through the optical coupler 575 and outputted through the exit hole of the main waveguide 570. As described above, since the resonance condition of the resonance waveguide 580 is changed in correspondence with concentration of the measured-material reacting at the interface of the opening 582 of the resonance waveguide 580, if intensity of the optical signal outputted through the exit hole of the main waveguide 570 is measured, a characteristic of the measured-material can be detected.

Figure 8:
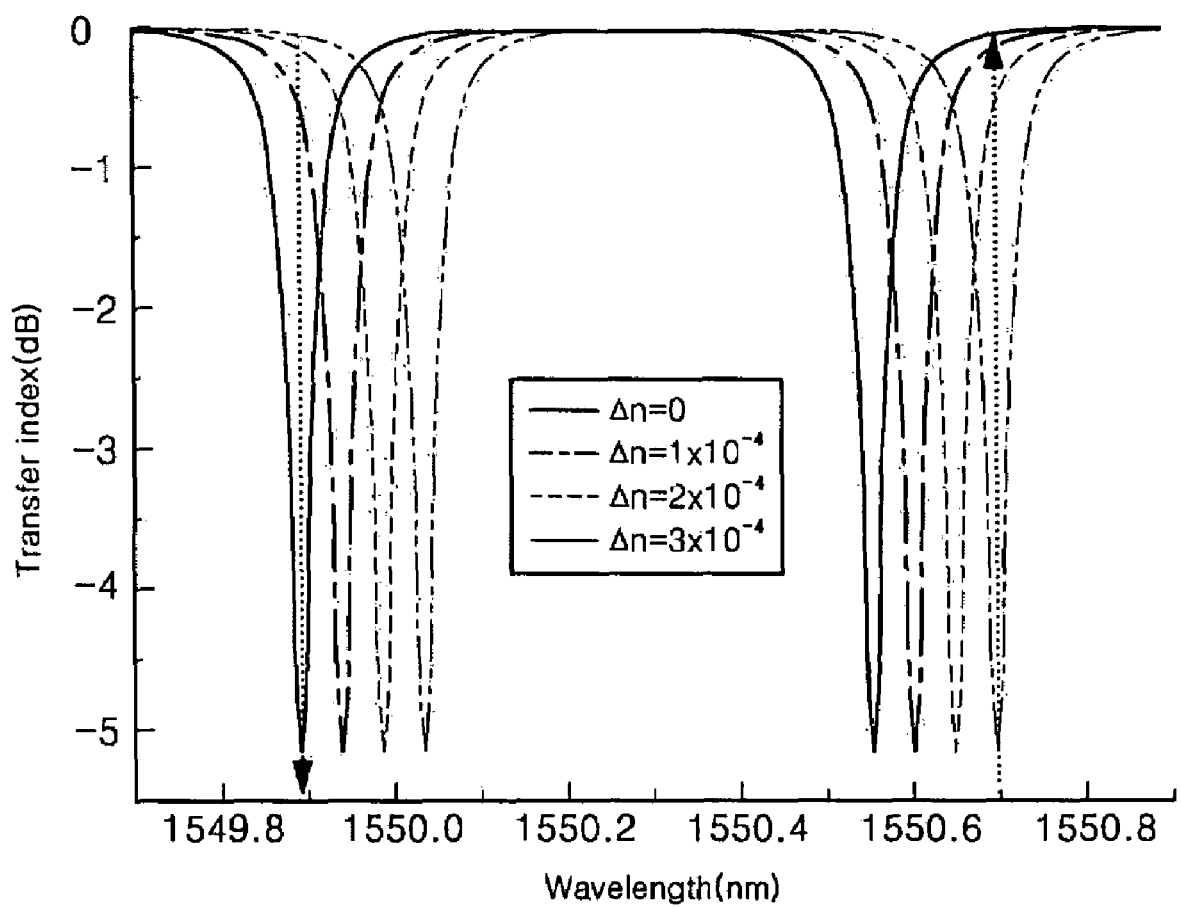
FIG. 8 is a view showing a signal detection method of a micro resonator sensor according to the invention.

FIG. 8 is a view showing a signal detection method of a micro resonator sensor according to the invention.

Referring to FIG. 8, in the micro resonator sensor described above referring to FIGS. 5 to 7, while the optical signal inputted through the incident hole of the main waveguide 510, 540, and 570 travels along the main waveguide 510, 540, and 570, only the optical signal having a wavelength satisfying the resonance condition of the resonance waveguide 520, 550, and 580 optically connected to the main waveguide 510, 540, and 570 are coupled to the resonance waveguide 520, 550, and 580. At this time, the refractive index of the resonance waveguide 520, 550, and 580 is changed depending on adhesiveness between the receptor and the measured-material (e.g., a bio material, or an environmental material) arranged at the opening 522, 524, 552, 554, and 582 formed at the resonance waveguide 520, 550, and 580. Such a change in the refractive index of the resonance waveguide 520, 550, and 580 induces a change in the phase of the optical signal circulating inside the resonance waveguide 520, 550, and 580, and thus the coupling resonance condition is changed. Therefore, among the optical signal inputted through the incident hole of the main waveguide 510, 540, and 570, the wavelength of an optical signal that is not coupled to the resonance waveguide 520, 550, and 580, but outputted through the exit hole of the main waveguide 510, 540, and 570 is changed.

A measurement unit (not shown) detects intensity of the optical signal outputted from the exit hole of the main waveguide 510, 540, and 570 through a photo detector such as a photo diode arranged at the exit hole of the main waveguide 510, 540, and 570. At this time, while the measured-material is not placed at the opening 522, 524, 552, 554, and 582 formed at the optical waveguides forming the resonance waveguide 520, 550, and 580, the measurement unit detects intensity of light having a wavelength corresponding to the resonance wavelength, which is a wavelength at which an optical signal is not detected at the exit hole of the main waveguide 510, 540, and 570 since the resonance condition between the main waveguide 510, 540, and 570 and the resonance waveguide 520, 550, and 580 is satisfied. Such a resonance wavelength exists at intervals corresponding to a free spectral range (FSR), and the measurement unit desirably detects intensity of an optical signal in the lower and upper directions at a plurality of resonance wavelengths (i.e., 1549.893 nm and 1550.698 nm) for further correct measurement. Next, based on the detected intensity of the optical signal, the measurement unit calculates variation of the effective refractive index of the resonance waveguide 520, 550, and 580 resulting from the measured-material placed at the opening 522, 524, 552, 554, and 582 formed at the optical waveguides configuring the resonance waveguide 520, 550, and 580.

If intensities of the optical signal are detected at a plurality of resonance wavelengths, the measurement unit calculates a value difference between the intensities of the optical signal detected at the resonance wavelengths (a value calculated by subtracting the intensity of light measured downward from a second resonance wavelength from the intensity of light measured upward from a first resonance wavelength) and calculates variation of the effective refractive index of the resonance waveguide 520, 550, and 580 based on value differences. Finally, the measurement unit grasps concentration of the measured-material placed at the opening 522, 524, 552, 554, and 582 formed at the optical waveguides configuring the resonance waveguide 520, 550, and 580 based on the calculated variation of the effective refractive index, thereby detecting a characteristic of the measured-material.

Figure 9:
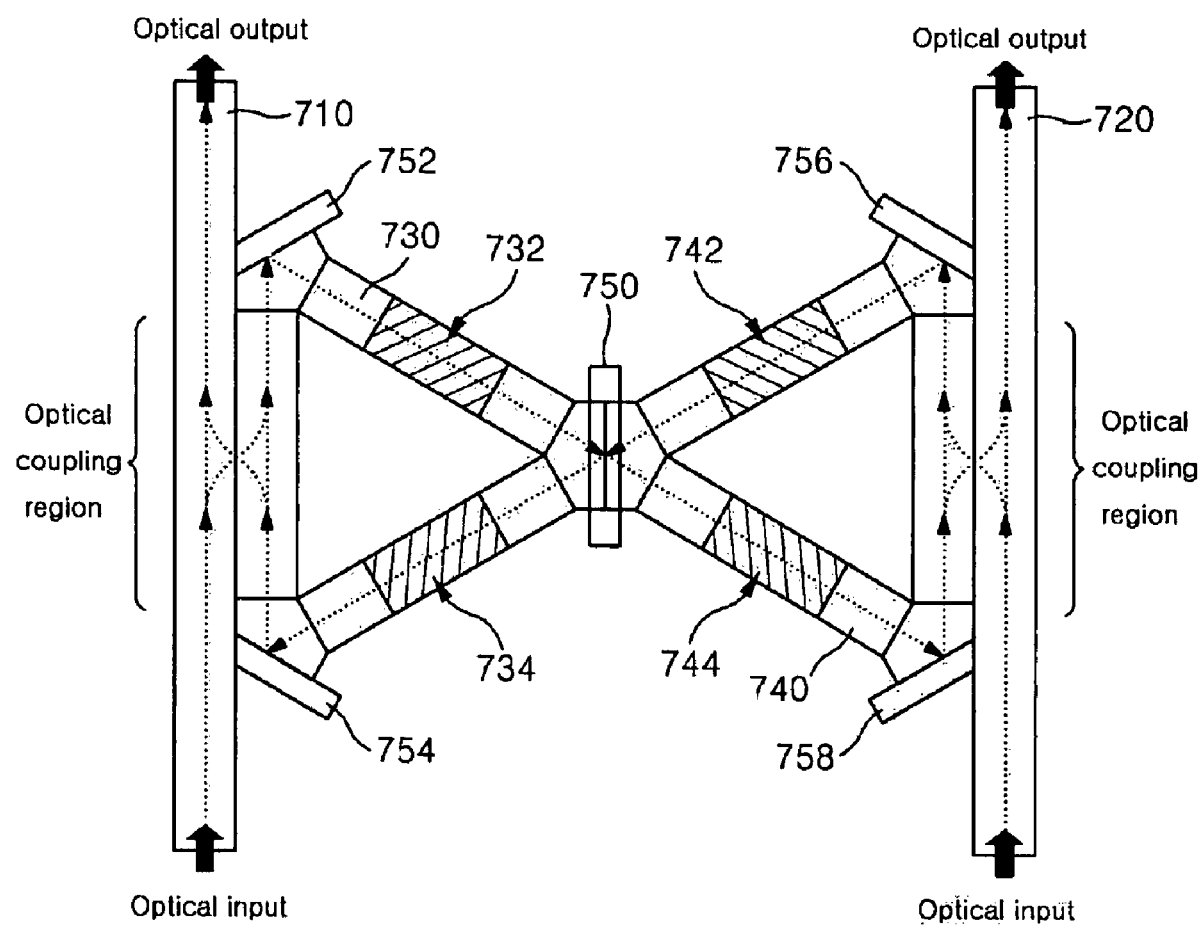
FIG. 9 is a view showing the configuration of a micro resonator sensor according to a fourth embodiment of the invention.

FIG. 9 is a view showing the configuration of a micro resonator sensor according to a fourth embodiment of the invention. The micro resonator sensor shown in FIG. 9 has a structure of connecting two micro resonator sensors shown in FIG. 6.

Referring to FIG. 9, the micro resonator sensor according to the fourth embodiment of the invention comprises a first main waveguide 710, a second main waveguide 720, a first resonance waveguide 730, a second resonance waveguide 740, a beam splitter 750, and total reflection mirrors 752, 754, 756, and 758. The micro resonator sensor shown in FIG. 9 has a structure of connecting two micro resonator sensors shown in FIG. 6 through the beam splitter 750. An optical signal inputted through the incident hole of the first main waveguide 710 is coupled to the first resonance waveguide 730 in the optical coupling region. The optical signal inputted into the first resonance waveguide 730 is reflected by a first total reflection mirror 752 installed at the first resonance waveguide 730 and advances to the beam splitter 750. The beam splitter 750 splits the inputted optical signal to the second total reflection mirror 754 installed at the first resonance waveguide 730 and to the second resonance waveguide 740. The optical signal inputted into the second resonance waveguide 740 is reflected by the fourth total reflection mirror 758 and the third total reflection mirror 756 installed at the second resonance waveguide 740 and circulates inside the second resonance waveguide. Then, the circulated optical signal is inputted into the beam splitter 750 again, and a part of the optical signal is coupled to the first resonance waveguide 730.

The optical signals inputted into the first resonance waveguide 730 and the second resonance waveguide 740 in the process of transferring optical signals described above respectively react with a measured-material of a liquid or gaseous state at the openings 732, 734, 742, and 744 formed at the first resonance waveguide 730 and the second resonance waveguide 740, and effective refractive indexes of the first resonance waveguide 730 and the second resonance waveguide 740 are changed in correspondence with concentrations of the to-be-measured materials reacting at the openings 732, 734, 742, and 744. If the effective refractive indexes of the two resonance waveguides 730 and 740 are changed, the condition of coupling from the first main waveguide 710 to the first resonance waveguide 730 is changed. Accordingly, since the amount of light outputted through the exit hole of the first main waveguide 710 is changed, characteristics of the materials can be detected. If a resonator is configured by connecting two resonance waveguides as shown in FIG. 9, the wavelength of an optical signal outputted through the main waveguide has an output form of a band-stop, not a band-pass, and thus it is advantageous in that a wide resonance interval can be obtained by a Vernier effect.

Figure 10:
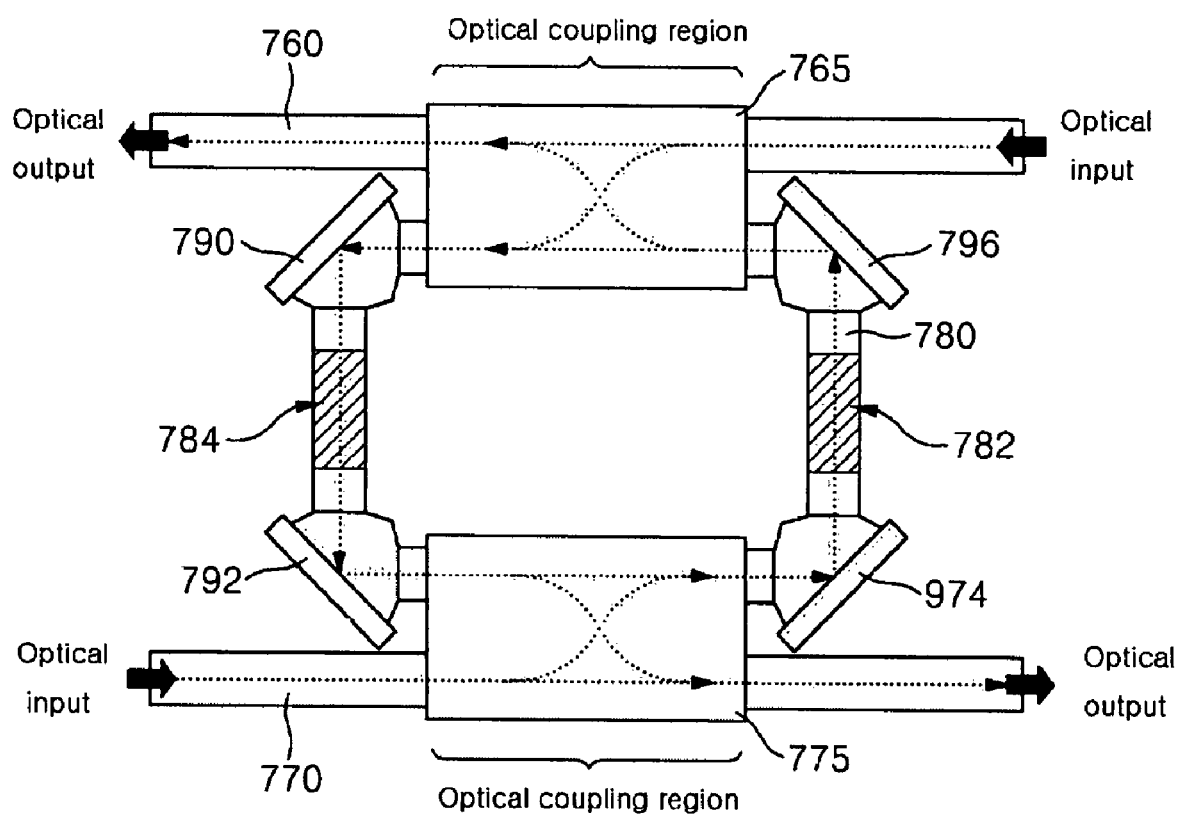
FIG. 10 is a view showing the configuration of a micro resonator sensor according to a fifth embodiment of the invention.

FIG. 10 is a view showing the configuration of a micro resonator sensor according to a fifth embodiment of the invention.

Referring to FIG. 10, the micro resonator sensor according to the fifth embodiment of the invention comprises a first main waveguide 760, a first optical coupler 765, a second main waveguide 770, a second optical coupler 775, a resonance waveguide 780, and total reflection mirrors 790, 792, 794, and 796.

An optical signal inputted through the incident hole of the first main waveguide 760 is coupled to the resonance waveguide 780 by the first optical coupler 765. The optical signal coupled to the resonance waveguide 780 is reflected by the first total reflection mirror 790 and the second total reflection mirror 792 arranged at the resonance waveguide 780 and inputted into the second optical coupler 775. The optical signal reflected by the second total reflection mirror 792 and inputted into the second optical coupler 775 is coupled to the second main waveguide 770 and outputted through the exit hole of the second main waveguide 770. In this process, the optical signal coupled to the resonance waveguide 780 reacts with a measured-material of a liquid or gaseous state at the opening 784 formed between the first total reflection mirror 790 and the second total reflection mirror 792. Accordingly, the effective refractive index of the resonance waveguide 780 is changed, and the phase of the optical signal is changed, and thus a coupling resonance condition is changed. Therefore, if intensity of the optical signal outputted through the exit hole of the second main waveguide 770 is measured, a characteristic of the measured-material can be detected. On the other hand, if an optical signal is inputted through the incident hole of the second main waveguide 770, the measured-material reacts with the optical signal at the opening 782 formed between the third total reflection mirror 794 and the fourth total reflection mirror 796 arranged at the resonance waveguide 780. In this case, a characteristic of the measured-material is detected by detecting intensity of the optical signal outputted through the exit hole of the first main waveguide 760. If a resonator is configured by connecting two resonance waveguides as shown in FIG. 10, the wavelength of an optical signal outputted through a main waveguide has an output form of a band-stop, not a band-pass.

Figure 11:
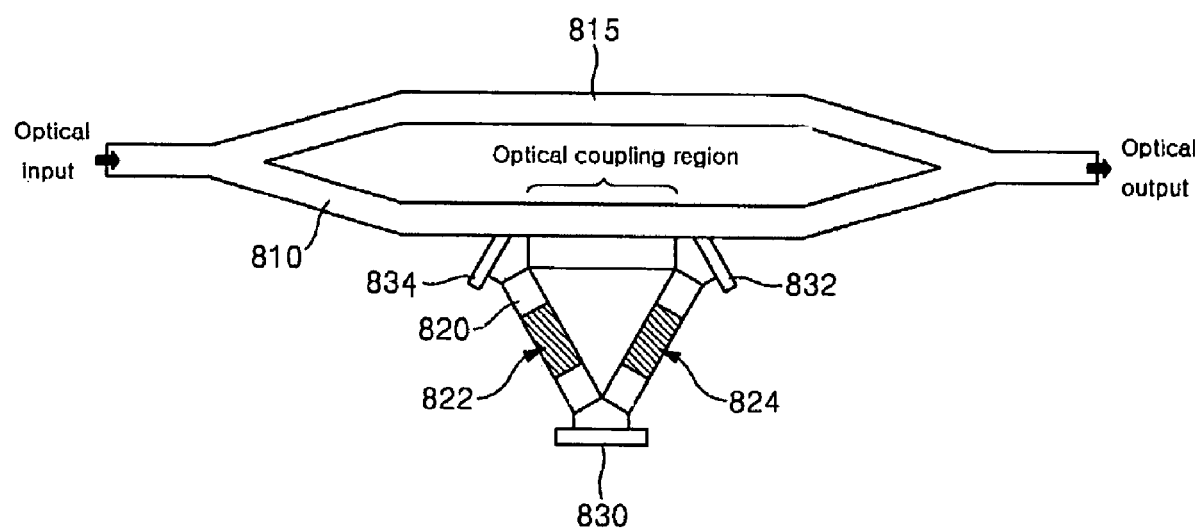
FIG. 11 is a view showing the configuration of a micro resonator sensor according to a sixth embodiment of the invention.

FIG. 11 is a view showing the configuration of a micro resonator sensor according to a sixth embodiment of the invention. The micro resonator sensor shown in FIG. 11 has a structure of connecting the micro resonator sensor of the second embodiment shown in FIG. 6 to a Mach-Zehnder electro-optic modulator.

Referring to FIG. 11, the micro resonator sensor according to the sixth embodiment of the invention has a structure of connecting a resonance waveguide 820 where total reflection mirrors 830, 832, and 834 are arranged at apexes to one optical waveguide 810 of two optical waveguides 810 and 815 configuring the Mach-Zehnder electro-optic modulator. An optical signal inputted into the input terminal of the Mach-Zehnder electro-optic modulator formed on an electro-optic material passes through the two optical waveguides 810 and 815. The optical signals passing through the two optical waveguides are combined again as one light, and the combined light is outputted to the exit hole. At this point, an optical signal inputted into one optical waveguide 810 is coupled to an optical waveguide configuring the resonance waveguide 820 arranged in parallel with the corresponding optical waveguide 810 and inputted into the resonance waveguide 820. The optical signal inputted into the resonance waveguide 820 is reflected by the total reflection mirrors 830, 832, and 834 arranged at the apexes of the resonance waveguide 820 and circulates inside the resonance waveguide 820.

The optical signal circulating inside the resonance waveguide 820 reacts with a measured-material of a liquid or gaseous state at the openings 822 and 824 formed between respective total reflection mirrors 830, 832, and 834, and the effective refractive index of the resonance waveguide 820 is changed in correspondence with concentration of the measured-material reacting at the openings 822 and 824. Due to the change of the effective refractive index of the resonance waveguide 820, the phase of the optical signal re-coupled from the resonance waveguide 820 to the optical waveguide 810 that is connected to the resonance waveguide 820 among the optical waveguides configuring the Mach-Zehnder electro-optic modulator is changed. Accordingly, since a constructive or destructive interference occurs between optical signals in correspondence with phase difference of the optical signals passing through two different optical waveguides 810 and 815 of the Mach-Zehnder electro-optic modulator formed on an electro-optic material, a characteristic of the measured-material can be detected by detecting intensity of the optical signal outputted through the exit hole of the Mach-Zehnder electro-optic modulator.

Figure 12:
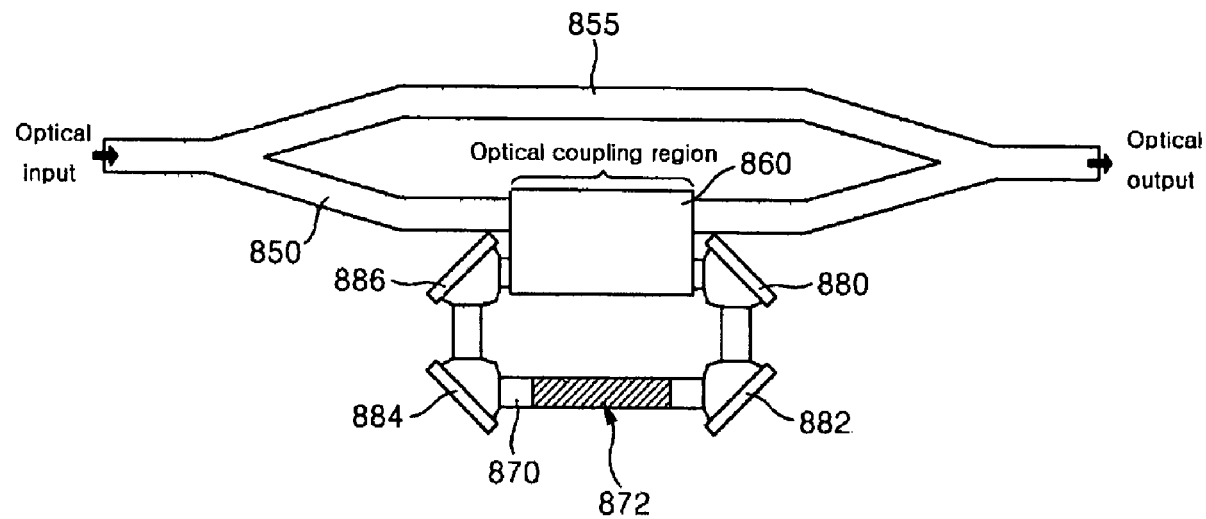
FIG. 12 is a view showing the configuration of a micro resonator sensor according to a seventh embodiment of the invention.

FIG. 12 is a view showing the configuration of a micro resonator sensor according to a seventh embodiment of the invention. The micro resonator sensor shown in FIG. 12 has a structure of connecting the micro resonator sensor of the third embodiment shown in FIG. 7 to a Mach-Zehnder electro-optic modulator.

Referring to FIG. 12, the micro resonator sensor according to the seventh embodiment of the invention has a structure of connecting a resonance waveguide 870 where total reflection mirrors 880, 882, 884, and 886 are arranged at apexes to one optical waveguide 850 of two optical waveguides 850 and 855 configuring the Mach-Zehnder electro-optic modulator through an optical coupler 860. An optical signal inputted into the input terminal of the Mach-Zehnder electro-optic modulator formed on an electro-optic material passes through the two optical waveguides 850 and 855. The optical signals passing through the two optical waveguides are combined again as one light, and the combined light is outputted to the exit hole. At this point, an optical signal inputted into one optical waveguide 850 is coupled to the resonance waveguide 870 through the optical coupler 860 connected to the corresponding optical waveguide 850. The optical signal inputted into the resonance waveguide 870 is reflected by the total reflection mirrors 880, 882, 884, and 886 arranged at apexes of the resonance waveguide 870 and circulates inside the resonance waveguide 870.

The optical signal circulating inside the resonance waveguide 870 reacts with a measured-material of a liquid or gaseous state at an opening 872 formed between the total reflection mirrors 882 and 884, and the effective refractive index of the resonance waveguide 870 is changed in correspondence with concentration of the measured-material reacting at the opening 872. Due to the change of the effective refractive index of the resonance waveguide 870, the phase of the optical signal re-coupled from the resonance waveguide 870 to the optical waveguide 850 that is connected, through the optical coupler 860, to the resonance waveguide 870 among the optical waveguides configuring the Mach-Zehnder electro-optic modulator is changed. Accordingly, since a constructive or destructive interference occurs between optical signals in correspondence with phase difference of the optical signals passing through two different optical waveguides 850 and 855 of the Mach-Zehnder electro-optic modulator formed on an electro-optic material, a characteristic of the measured-material can be detected by detecting intensity of the optical signal outputted through the exit hole of the Mach-Zehnder electro-optic modulator.

Figure 13:
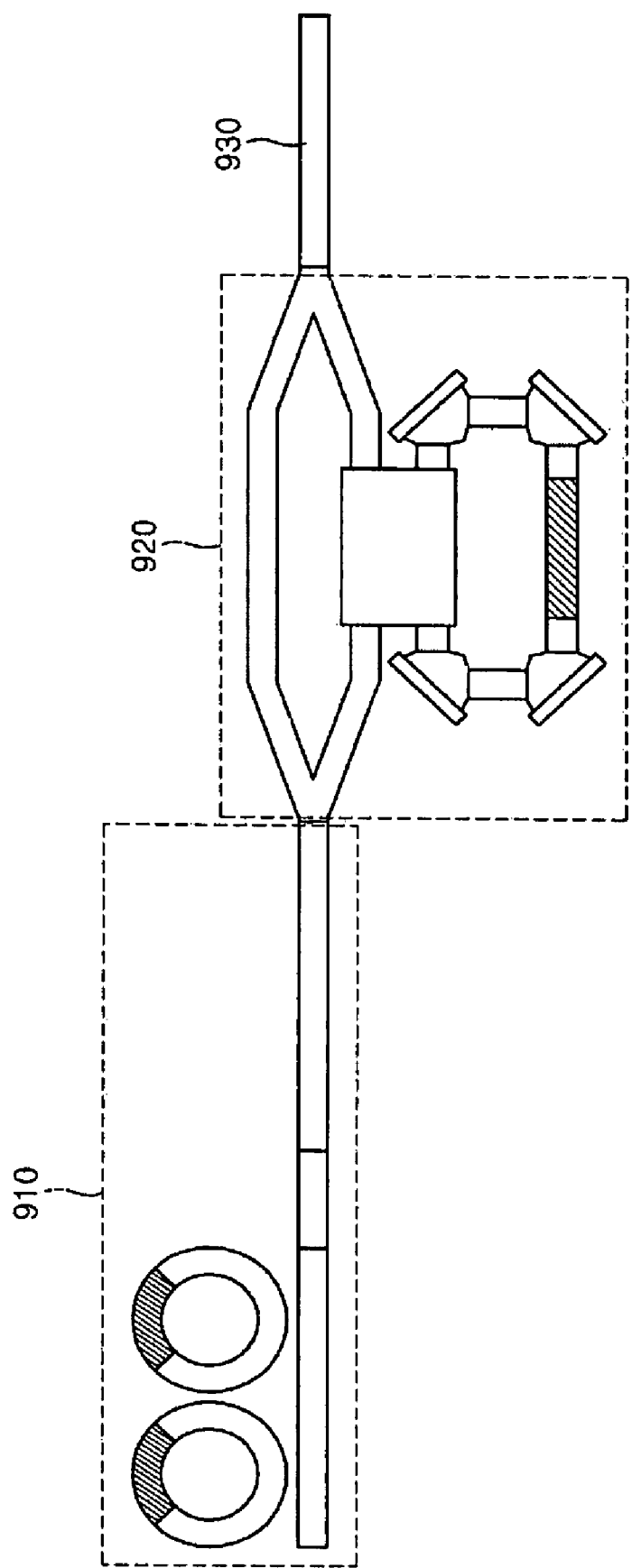
FIG. 13 is a view showing the configuration of a micro resonator sensor according to an eighth embodiment of the invention, which is formed by connecting a variable wavelength optical source and a photo detector to the seventh embodiment of the micro resonator sensor shown in FIG. 12.

FIG. 13 is a view showing the configuration of a micro resonator sensor according to an eighth embodiment of the invention, which is formed by connecting a variable wavelength optical source and a photo detector to the seventh embodiment of the micro resonator sensor shown in FIG. 12. The micro resonator sensor of the eighth embodiment shown in FIG. 13 is a sensor module structure comprising a light generation unit 910, a resonance unit 920, and a light detection unit 930, which are integrated on the same wafer by a photonic integrated circuit (PIC) technique. Such a micro resonator sensor can be manufactured in a super-micro size, and thus can be applied to a handheld apparatus. Since a plurality of resonators having a different size is integrated and a multiple wavelength can be applied, a multiple sensor can be implemented. Furthermore, although the micro resonator sensor according to the seventh embodiment of the present invention described referring to FIG. 12 is employed as the resonance unit 920 in FIG. 13, the micro resonator sensors according to the first to sixth embodiments of the present invention also can be employed as the resonance unit 920.

Accordingly, a ring resonator sensor of a super-micro size can be manufactured, and an optical source and a detector can be integrated as an on-chip on the same wafer, and therefore, the ring resonator sensor can be applied to bio-environment sensors and medical application fields.

According to the micro resonator sensor of the present invention, a resonator is configured using a total reflection mirror, and thus the micro resonator sensor can be manufactured without an excessive radiation loss. Furthermore, all elements can be integrated on the same wafer, and thus the micro resonator sensor can be manufactured as an on-chip. Therefore, it is advantageous in that a super-micro optical sensor module applicable to a handheld terminal can be manufactured.

Although the present invention has been described with reference to several preferred embodiments, the description is illustrative of the invention and is not to be construed as limiting the invention. Various modifications and variations may occur to those skilled in the art, without departing from the scope of the invention as defined by the appended claims.

What is claimed is:

1. A micro resonator sensor comprising:
   a main waveguide provided with an incident hole for receiving an optical signal and an exit hole for outputting an optical signal, having an optical coupling region where a part of the optical signal inputted through the incident hole is split;
   a resonance waveguide having an optical coupling region optically connected to the optical coupling region of the main waveguide to receive the split optical signal split from the main waveguide, the resonance waveguide being configured of a plurality of optical waveguides arranged in a polygonal shape; and
   optical path changing means installed at apex regions contacting adjacent optical waveguides forming the resonance waveguide, for reflecting at least a part of the split optical signal inputted into the resonance waveguide to circulate the split optical signal inside the resonance waveguide, wherein openings are formed at one or more optical waveguides among optical waveguides configuring the resonance waveguide.

2. The sensor according to claim 1, wherein the optical coupling region of the main waveguide and the optical coupling region of the resonance waveguide are formed as a single body together with an optical waveguide configuring the main waveguide, and the optical path changing means includes:
   optical split elements installed at both ends of the optical coupling region, for splitting the optical signal inputted through the incident hole toward the exit hole of the main waveguide and toward the resonance waveguide; and
   a total reflection element installed at the apex region contacting with optical waveguides other than an optical waveguide corresponding to the optical coupling region among the optical waveguides configuring the resonance waveguide, for totally reflecting the inputted split optical signal.

3. The sensor according to claim 2, further comprising a subsidiary waveguide arranged in parallel with the main waveguide, wherein one end of the subsidiary waveguide is optically connected to the incident hole of the main waveguide, and the other end of the subsidiary waveguide is optically connected to the exit hole of the main waveguide.

4. The sensor according to claim 2, further comprising a monitoring unit for monitoring an optical signal outputted from an optical waveguide, among the optical waveguides configuring the resonance waveguide, connected to an optical split element installed at an incident hole side of the main waveguide among the optical split elements.

5. The sensor according to claim 1, wherein the optical path changing means are total reflection mirrors installed at the apex regions contacting with adjacent optical waveguides configuring the resonance waveguide to totally reflect the inputted split optical signal.

6. The sensor according to claim 1, further comprising an optical coupling element for splitting or coupling the inputted optical signal, wherein the optical coupling region of the main waveguide and the optical coupling region of the resonance waveguide are optically connected to the optical coupling element respectively, and the optical path changing means are total reflection mirrors installed at the apex regions contacting with adjacent optical waveguides configuring the resonance waveguide to totally reflect the inputted split optical signal.

7. The sensor according to claim 1, further comprising a subsidiary waveguide arranged in parallel with the main waveguide, wherein one end of the subsidiary waveguide is optically connected to the incident hole of the main waveguide, and the other end of the subsidiary waveguide is optically connected to the exit hole of the main waveguide.

8. The sensor according to claim 1, wherein the optical waveguides configuring the resonance waveguide have a cross-section of a rectangular shape, and the openings are formed on at least one of a top surface and side surfaces of the optical waveguides configuring the resonance waveguide.

9. The sensor according to claim 1, further comprising a measurement unit for detecting intensity of light outputted from the exit hole of the main waveguide and calculating variation of an effective refractive index of the resonance waveguide through to-be-measured materials placed at the openings formed at the optical waveguides configuring the resonance waveguide.

10. The sensor according to claim 9, wherein the measurement unit detects intensities of light having wavelengths corresponding to a plurality of wavelengths having intervals corresponding to integer times of a free spectral range (FSR) and calculates the variation of the effective refractive index of the resonance waveguide based on value differences of the detected intensities of the light.

11. The sensor according to claim 9, further comprising an optical source unit for generating an optical signal and inputting the generated optical signal into the incident hole of the main waveguide.

12. The sensor according to claim 11, wherein the optical source unit comprises:
   an optical source for outputting the optical signal;
   a first resonance ring configured of an optical waveguide of a circular shape having a first radius, the optical waveguide being formed with a phase control region where a refractive index is changed depending on the amount of driving current supplied from outside;
   a second resonance ring configured of an optical waveguide of a circular shape having a second radius, the optical waveguide being formed with a phase control region where a refractive index is changed depending on the amount of driving current supplied from outside; and
   an optical waveguide arranged to be spaced apart from the first resonance ring and the second resonance ring, for changing a wavelength of an optical signal outputted from the optical source in correspondence with the variation of the refractive index of the first resonance ring or the second resonance ring.

13. The sensor according to claim 11, wherein the optical source, the main waveguide, the resonance waveguide, the optical path changing means and the measurement unit are integrated on a single wafer and manufactured as a photonic integrated circuit.

14. A micro resonator sensor comprising:
   a first main waveguide provided with an incident hole for receiving an optical signal and an exit hole for outputting an optical signal, the first main waveguide having an optical coupling region where a part of the optical signal inputted through the incident hole is split;
   a first resonance waveguide having an optical coupling region optically connected to the optical coupling region of the first main waveguide to receive the split optical signal split from the first main waveguide, the first resonance waveguide being configured of a plurality of optical waveguides arranged in a polygonal shape;
   a second main waveguide provided with an incident hole for receiving an optical signal and an exit hole for outputting an optical signal, the second main waveguide having an optical coupling region where a part of the optical signal inputted through the incident hole is split;
   a second resonance waveguide having an optical coupling region optically connected to the optical coupling region of the second main waveguide for receiving the split optical signal split from the second main waveguide, the second resonance waveguide being configured of a plurality of optical waveguides arranged in a polygonal shape; and
   optical path changing means installed at apex regions contacting with adjacent optical waveguides forming the first and second resonance waveguides, for reflecting at least a part of the split optical signal inputted into the first or second resonance waveguide to circulate the split optical signal inside the first and second resonance waveguides, wherein the first and second resonance waveguides form a single resonance path by sharing one apex, and openings are formed at one or more optical waveguides among optical waveguides configuring the first and second resonance waveguides.

15. The sensor according to claim 14, wherein the optical coupling region of the first main waveguide and the optical coupling region of the first resonance waveguide are formed as a single body together with an optical waveguide configuring the first main waveguide, and the optical coupling region of the second main waveguide and the optical coupling region of the second resonance waveguide are formed as a single body together with an optical waveguide configuring the second main waveguide, and the optical path changing means includes:

first optical split elements installed at both ends of the optical coupling region, for splitting the optical signal inputted through the incident hole toward the exit holes of the first and second main waveguides and toward the first and second resonance waveguides; and a second optical split element installed at an apex region shared by the first and second resonance waveguides, for providing a split optical signal inputted into the first resonance waveguide to the second resonance waveguide and providing a split optical signal inputted into the second resonance waveguide to the first resonance waveguide;

total reflection elements installed at apex regions contacting with optical waveguides other than optical waveguides corresponding to the optical coupling regions among the optical waveguides configuring the first and second resonance waveguides, for totally reflecting an inputted split optical signal.

16. The sensor according to claim 14, wherein the optical path changing means includes:

an optical split element installed at an apex region shared by the first and second resonance waveguides, for providing a split optical signal inputted into the first resonance waveguide to the second resonance waveguide and providing a split optical signal inputted into the second resonance waveguide to the first resonance waveguide;

total reflection mirrors installed at apex regions contacting with adjacent optical waveguides configuring the first and second resonance waveguides, for totally reflecting inputted split optical signal.

17. The sensor according to claim 14, further comprising:

a first optical coupling element for optically connecting the optical coupling region of the first main waveguide and the optical coupling region of the first resonance waveguide;

a second optical coupling element for optically connecting the optical coupling region of the second main waveguide and the optical coupling region of the second resonance waveguide, wherein the optical path changing means includes:

an optical split element installed at the apex region shared by the first and second resonance waveguides, for providing a split optical signal inputted into the first resonance waveguide to the second resonance waveguide and providing a split optical signal inputted into the second resonance waveguide to the first resonance waveguide;

a total reflection mirror installed at the apex region contacting with each of the optical waveguides configuring the resonance waveguide, for totally reflecting an inputted split optical signal.

18. The sensor according to claim 14, wherein the optical waveguides configuring the first and second resonance waveguides has a cross-section of a rectangular shape, and the openings are formed on at least one of a top surface and side surfaces of the optical waveguides configuring the first and second resonance waveguides.

19. The sensor according to claim 14, further comprising a measurement unit for detecting intensity of light outputted from the exit hole of the first or second main waveguide and calculating variation of an effective refractive index of the first or second resonance waveguide through a to-be-measured materials placed at the openings formed at the optical waveguides configuring the first or second resonance waveguide.

20. The sensor according to claim 19, wherein the measurement unit detects intensities of light having wavelengths corresponding to a plurality of wavelengths having intervals corresponding to integer times of a free spectral range (FSR) and calculates the variations of the effective refractive indexes of the first and second resonance waveguides based on value differences of the detected intensities of the light.

* * * * *